United States Patent [19]
Beeuwkes, III; Reinier

[11] Patent Number: 5,456,703
[45] Date of Patent: Oct. 10, 1995

[54] APPARATUS FOR APPLICATION OF HEAT/COLD TO TARGET REGIONS OF THE HUMAN ANATOMY

[75] Inventor: Reinier Beeuwkes, III, Concord, Mass.

[73] Assignee: Therabite Corporation, Newtown Square, Pa.

[21] Appl. No.: 288,437

[22] Filed: Aug. 10, 1994

Related U.S. Application Data

[63] Continuation of Ser. No. 55,146, Apr. 28, 1993, abandoned.

[51] Int. Cl.$^6$ ..................................... A61F 7/00
[52] U.S. Cl. ........................ 607/109; 607/112; 607/114
[58] Field of Search .................. 607/96, 104, 108–112, 607/114; 128/746

[56] References Cited

U.S. PATENT DOCUMENTS

| | | | |
|---|---|---|---|
| 919,614 | 4/1909 | Meinecke. | |
| 1,252,285 | 1/1918 | Manley | 607/114 |
| 1,488,743 | 4/1924 | Eggers | 607/112 |
| 1,634,373 | 7/1927 | Mann | 607/96 X |
| 2,249,790 | 7/1941 | Schwyn | 607/109 |
| 2,933,086 | 4/1960 | Gray. | |
| 3,349,825 | 10/1967 | Andreadis. | |
| 3,768,485 | 10/1973 | Linick | 607/109 |
| 3,796,855 | 3/1974 | Brown et al. | 607/108 X |
| 4,243,041 | 1/1981 | Paul. | |
| 4,376,437 | 3/1983 | Sundheim et al. | 607/104 X |
| 4,466,438 | 8/1984 | Katz | 128/746 |
| 4,466,439 | 8/1984 | Moore | 607/109 |
| 4,570,635 | 2/1986 | Henig. | |
| 4,674,134 | 6/1987 | Lundin. | |
| 4,706,673 | 11/1987 | Meistrell | 607/114 X |

FOREIGN PATENT DOCUMENTS

| | | | |
|---|---|---|---|
| 1666076 | 7/1991 | U.S.S.R. | 607/114 |

*Primary Examiner*—Angela D. Sykes
*Attorney, Agent, or Firm*—Bush, Moseley, Riddle & Jackson

[57] ABSTRACT

Apparatus is provided for applying heat/cold to selected target regions of the human anatomy such as the temporalis and masseter muscles and to the region of the temporomandibular joint of the human cranial anatomy as well as other selected regions of the human anatomy such as the shoulders, knees, etc. At least one heat/cold compliant thermal cell is defined by a rigid back having a thin and compliant membrane connected thereto and defining a chamber for containing a substantial volume of a liquid or semi-liquid such as water or a gel, at a preselected temperature. The rigid back or shell defines a circumferential rim to which the compliant membrane is secured. The compliant membrane may have a side wall portion extending in substantially contiguous relation from the rim of the rigid shell and incorporates an integral substantially planar front wall portion which establishes intimate face-to-face heat/cold transferring relation with an anatomical target region. The membrane will engage the target region with low pressure per unit area and thus will readily conform to the configuration of the target region. The rigid shell defines a liquid inlet/outlet opening which is provided with a removable closure enabling heated or cooled liquid to be poured into or from the internal compartment. The thermal cell may include a heating or cooling system to enable prolonged therapeutic use. The thermal cell is adapted for releasable assembly with a support device such as a headband so that therapy may be conducted in hands-free manner. The headband assembly provides for a wide range of adjustment for selective location of the thermal cell and also provides substantially omnidirectional support so that the thermal cell can be readily oriented in conformance with the anatomical target region.

17 Claims, 4 Drawing Sheets

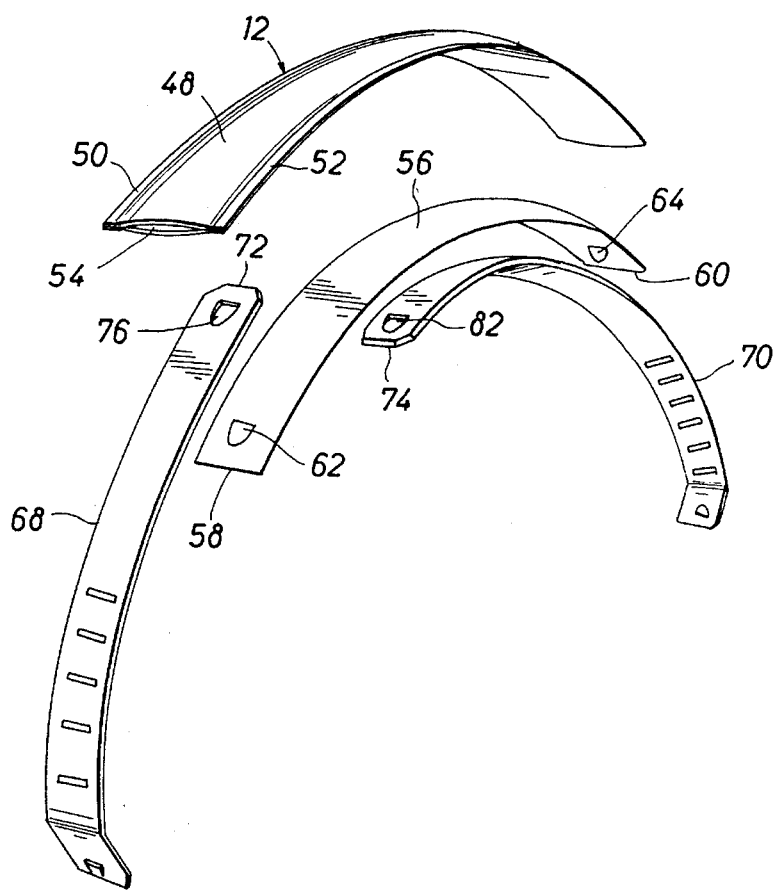

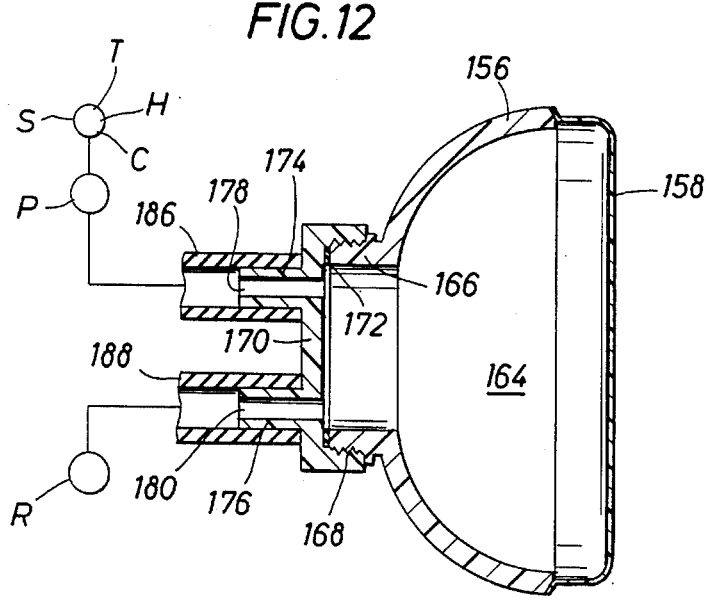
FIG.12
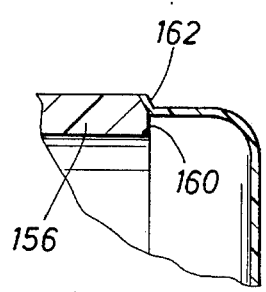
FIG.13
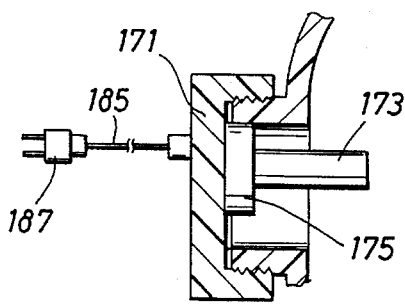
FIG.12a
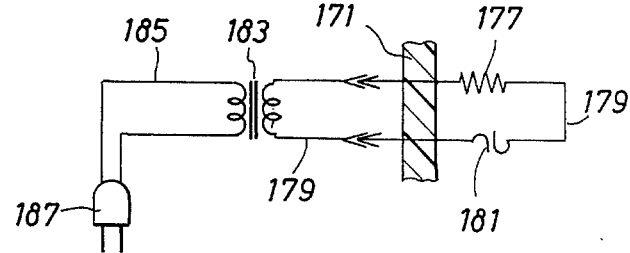
FIG.12b
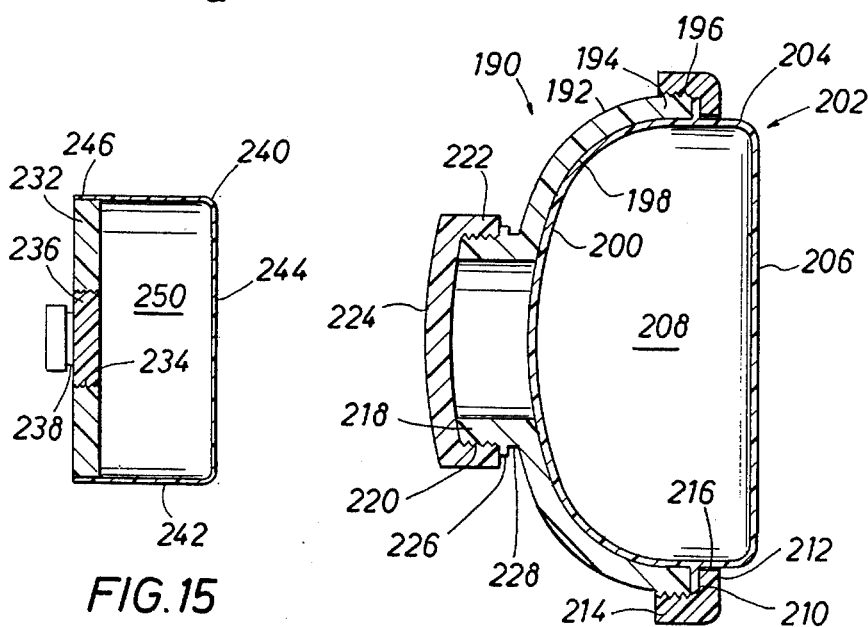
FIG.15
FIG.14

APPARATUS FOR APPLICATION OF HEAT/COLD TO TARGET REGIONS OF THE HUMAN ANATOMY

This application is a continuation of application Ser. No. 07/055,146 filed Apr. 28, 1993, now abandoned.

FIELD OF THE INVENTION

This invention relates generally to a method and apparatus for therapeutic treatment by application of heat or cold to target regions of the human body. More specifically, the present invention concerns the provision of apparatus for selective application of heat or cold to selected regions of the human body such as the temporalis and masseter muscles and to the area immediately surrounding the temporomandibular joint (TMJ) while permitting the use of a mandible mobilizer and/or other therapeutic devices or techniques. Even more specifically, the present invention concerns a thermal cell which is heated or cooled by an internal medium or by a heating or cooling system and which is selectively utilized for application of heat or cold to any selected region of the body.

BACKGROUND OF THE INVENTION

The present invention, for the sake of simplicity is discussed herein particularly as it relates to therapeutic activity following maxillo-facial surgery. It should be borne in mind however, that the inventor has many other uses within the scope thereof.

Especially in the case of maxillo-facial surgery, the mandible is typically immobilized with respect to the maxilla such as by means of various types of retainer devices such as retainer wires, retainer bands, etc. to stabilize the bone structure and to maintain dentition in desired occlusion during healing of the bone structure. After an extended period of mandibular immobilization the temporalis and masseter muscles tend to become atrophied and the temporo-mandibular joint may become somewhat seized or restricted. In order to restore the mandible to its normal range of movement about the temporo-mandibular joint, the patient is normally required to undergo a therapeutic procedure where the mandible is forcibly operated by means of a mobilizer and/or by means of any of a number of other therapeutic devices. It has been found helpful in the restoration of the temporalis and masseter muscles to the normal range of extension and contraction, to apply heat or cold to the region of the temporalis and masseter muscles as well as to the region of the temporo-mandibular joint, either before, during or after mandible mobilizing therapy. It is considered desirable, therefore, to provide a suitable means for selective application of heat or cold to these specific facial areas and to provide the heat and cold in such manner so as not to interfere with normal therapeutic activities.

Many medical and dental patients are known to encounter difficulty, pain sensation, etc. with respect to the temporomandibular joint and in some cases, the sinuses in the region of the TMJ. It is well known that the selective application of heat and/or cold in accordance with a desired therapeutic sequence can yield effective relief to the patient. In most cases heat or cold is applied by positioning a heat pack or ice pack in engaging relation with the region of the TMJ or the temporalis and masseter muscles. This is typically a cumbersome and time consuming procedure especially because the patient must hold the apparatus in place or must tape it to the body. It is desirable therefore, to provide therapeutic means for selective application of heat or cold to the cranial region of the temporalis and masseter muscles and TMJ through means that is supported entirely by the head of the patient and which therefore permits the patient to accomplish other tasks and to conduct other activities while undergoing heat/cold therapy.

The cranial anatomy in the region of the temporalis and masseter muscles and the region of the TMJ, though being fairly smooth, nevertheless provides projections and depressions. To adequately deliver therapeutic heat or cold to this region, it is for the most part appropriate to maintain sufficient forcible contact of the heat pack or ice pack with the target region of the cranial anatomy such that efficient heat transfer is made. It is desirable, therefore, to provide a therapeutic system for application of heat or cold which is capable of establishing efficient heat transferring, surface-to-surface relation with the target region of the cranial anatomy while at the same time requiring application of only minimal mechanical force against facial surfaces to thereby permit the patient to undergo efficient heat or cold therapy in such manner as to be free from the pain or discomfort that might be caused if the mechanical force that is necessary if heat transfer were localized. It is desirable, for the comfort of the user to engage the target-region with a low pressure force per unit area and yet achieve efficient heat transfer to the target region.

In some cases physical therapy by means of therapeutic application of heat or cold may require periodic application of heat followed by periodic application of cold during any given therapy procedure. It is desirable, therefore, to provide a suitable means for accomplishing simple, quick and efficient change of the therapeutic application of heat or cold to a target region of the cranial anatomy simply by switching the heat or cold applicators or refilling internal compartments that provide for heat or cold transfer to the target region. It is further desirable to provide means for therapeutic application of heat or cold to the cranial anatomy that permits virtually any patient, regardless of the patient's manual dexterity, to simply and efficiently conduct heat or cold therapy themselves, without necessitating close attention by a therapist and perhaps while the patient is conducting self therapy in the home or at a location away from the attention of any medical personnel. For example, for the relief of sinus pain or for thermal restorative therapy following maxillo-facial surgery self-therapy may be conducted while riding in any sort of conveyance, while at home or work, even while sleeping. Thermal therapy of this nature is not limited to the cranial region of the human anatomy. For example, thermal therapy of the shoulders, ankles, knees, elbows, etc. may also be treated through use of the present invention.

From the standpoint of heat/cold application to the cranial anatomy areas of frequent pain, especially following maxillofacial surgery, include the temporalis muscles just above and slightly forward of the ear and the sinuses in the region of the temporalis muscles. The masseter muscles located below and slightly forward of the ear are also sources of pain as are the tempor-mandibular joints at the bottom and slightly forward of the ears. Since all of these "target regions" of the cranial anatomy benefit from heat/cold therapy, it is desirable to provide thermal cells to be supported by a suitable support, such as a headband or support band and which has sufficient adjustability for selective positioning of the thermal cells at widely spaced target regions such as the temporalis and masseter muscles. Additionally, it is desirable to provide thermal cells of appropriate configuration for adequate coverage of selected target regions and to provide for substantially omnidirectional movement of the thermal cells relative to the support structure, i.e. rotation, pivoting etc. to enable the thermal cells to achieve intimate heat/cold transmitting relation with the target region.

The use of "water bottles" for application of heat or cold to the human body is quite well known. Water bottles are typically completely flexible devices, except for the filling opening thereof. Their use for therapeutic purposes has certain shortcomings which are considered as follows: If a hot water bottle is filled to the point that it is completely distended then it can be applied to a body surface in any position such as from the top down, from the side or from the bottom up. Being rigidly filled and distended however, hot water bottles will only conform intimately to a body surface by application of substantial mechanical pressure; enough pressure to cause elastic deformation of the flexible container. This significant mechanical pressure however can cause discomfort to the user and can result in interruption of or interference with capillary blood flow in the body tissues adjacent the contacted body surface. Interruption or interference with the capillary blood flow significantly retards the capability of the heat transfer to penetrate beneath the skin to other tissues for which therapy may be desired. It is desirable therefore to maintain intimate contact with a selected body surface for efficient heat transfer thereto and to ensure that application of mechanical force is maintained sufficiently low that efficient capillary blood flow can transport heat or cold to the selected tissues for therapeutic purposes.

If a conventional hot water bottle is filled to less than its capacity then it may be applied only downwardly against the target surface so as to utilize the assistance of gravity to establish intimate contact of its heat transferring surface with the body surface. When applied downwardly in this manner the hot water bottle, being only partly filled, will conform intimately to the body surface by bending and without stretching. No mechanical pressure is required in addition to the gravitational force that maintains the heat transferring surface in intimate surface conforming contact with the body surface.

If an attempt is made to apply a hot water bottle filled to less than capacity sideways against a body surface gravity will cause the fluid within the hot water bottle to descend to the lower portion of the container, i.e. slumping downwardly. This causes the vertical, body contacting surface to establish poor conformity with the body surface and to establish only partial contact of the heat transferring fluid contained therein to the heat transferring surface. Obviously the result is poor heat transferring capability and difficulty of controlling application of heat or cold to a selected target region. Any attempt to push on the side of the flexible hot water bottle container with a retainer of small dimension merely accomplishes displacement of the thermal medium laterally and causes the force application of the small retainer to come into nearly direct contact with the skin tissue. Thus hot water bottles are only functionally efficient if they are applied to the body surface by means of a force that encompasses significant surface area, such as pushing against the hot water bottle with the entire hand of the user. Similarly, when a hot water bottle filled less than capacity is applied to the body tissue from an underside position, the deflection is similar but more pronounced. Thus when a small force applying device is used to hold a hot water bottle against the skin surface from the underside only the central portion of the hot water bottle will engage the skin and peripheral portions will descend downwardly due to gravitational force so that the only area of the hot water bottle in contact with the skin surface is quite small in comparison with its overall dimension. It is desirable therefore to provide a thermal cell construction having a compliant thermal transfer surface of large dimension and yet having the capability of engagement with a target anatomical surface with low internal pressure and low applied mechanical pressure or force in such a manner that the heat transferring surface conforms intimately with the contacted body surface and establishes efficient heat transferring contact therewith while maintaining a low force per unit area contact with the target surface.

SUMMARY OF THE INVENTION

It is a principal feature of the present invention to provide a novel heat/cold therapeutic cell that is capable of engaging a target anatomical region with low mechanical pressure per unit area and yet achieving efficient heat transfer from the thermal cell to the target region.

It is another feature of this invention to provide a novel thermal cell mechanism for application of heat or cold therapy to an anatomical region such as the temporalis and masseter muscles and to the area immediately surrounding the tempero-mandibular joint (TMJ) while simultaneously permitting the use of a mandible mobilizer and other therapeutic devices and/or techniques.

It is an even further feature of this invention to provide a novel thermal cell and cell support mechanism for application of heat or cold therapy which may be easily and simply utilized by most any patient, regardless of the manual dexterity thereof, for conducting self-therapy.

It is another feature of this invention to provide a novel thermal cell heat/cold transfer system which can be completely portable, permitting the user to move about freely during therapeutic activities.

It is also a feature of this invention to provide a novel heat or cold therapeutic system having sufficient adjustability to provide a patient with the capability of applying heat or cold to the temporalis and masseter muscles and to the region of the TMJ or to other suitable anatomical regions in such manner that these regions, which may be sensitive to mechanical pressure, may receive efficient transfer of heat or cold thereto without subjecting the patient to the discomfort of localized high mechanical pressure.

It is another important feature of this invention to provide a novel heat or cold therapy system wherein heat and cold may be applied alternatively simply by changing out heat or cold thermal cells which are interconnected for efficient positioning and support by means of a quickrelease type support mechanism.

It is also a feature of this invention to provide a novel mechanism for application of heat or cold therapy by means of a thermal cell having a generally rigid shell with a compliant wall thereof defined by a heat transfer membrane having the capability of assuming efficient low mechanical pressure per unit area surface-to-surface engagement with the target region by easily conforming to the configuration of the target region while maintaining mechanical pressure therewith to a minimum for the purpose of comfort.

It is an even further feature of the present invention to provide a novel heat/cold therapy mechanism including heated or cooled compliant cells which may be heated or cooled by liquid interchange or which may be heated or cooled electrically or chemically as suits the needs of the user.

Briefly, the various features of the present invention are realized through the provision of at least one, and preferably a pair of compliant heat/cold thermal cells for transfer of heat or cold to target regions of the cranial anatomy, particularly the TMJ, the temporalis muscles or the masseter muscles of a patient or to other selected anatomical regions of the user. Each of the compliant heat/cold thermal cells will typically contain a liquid or semi-liquid heat transfer material having a low internal pressure, i.e. substantially atmospheric pressure, to thereby enable its heat/cold transferring surface to establish intimate contact with the body surface defining the target region to which the heat/cold is to be applied for therapeutic purposes. This low applied pressure and force enables efficient heat/cold transfer to take place for the comfort of the user and to ensure that the force of the heat transferring surface against the target region does not interfere with local blood flow. The heat transferring surface of the thermal cell conforms intimately to the surface of the target region and, by virtue of its construction, the thermal cell can be applied to the target region in any desired position. The apparatus also incorporates means for releasably securing or positioning the compliant cell or cells in intimate low mechanical pressure per unit area surface conforming contact with selected target regions of the selected anatomical region. This retention apparatus may conveniently take the form of a support band structure such as a headband, for example, from which the compliant cells are pivotally, rotatably and adjustably supported. Preferably the compliant cells are connected in assembly with the support band by means of omnidirectional connectors to thus permit the compliant cells to readily seek positions of optimum, intimate surface-to-surface contact with the target region depending upon the particular surface configuration of the target region.

According to the present invention a compliant thermal cell is provided for establishing efficient heat/cold transferring relation with a selected body surface. When in contact with the body surface. When in contact with the body surface the thermal cell maintains a low internal pressure, i.e. only slightly above atmospheric pressure and yet establishes intimate surface conforming contact with a selected body surface. By contacting the body surface with low mechanical pressure by virtue of the low internal fluid pressure of the thermal cell a large heat transferring surface of the thermal cell establishes intimate conforming contact with the target surface and thus can be comfortably used without causing any interference with local blood flow in the skin and adjacent body tissues. Additionally, the thermal cells construction enables the heat transferring surface to contact the body surface in any suitable position without the numerous deficiencies that are noted above in connection with conventional "hot water bottles". The container for the thermal fluid is exceptionally thin and quite flexible, though not necessarily elastic. This feature enhances the capability of the thermal cell to conform efficiently to the surface of the target region. When applied downwardly, gravity makes the contact of the heat transferring surface both broad and gentle. When applied vertically the rigid back structure of the thermal cell causes applied force to be distributed broadly across nearly the whole contact surface. The attachment or constraint of the flexible part of the container at the periphery prevents excessive lateral bulging. Thus, the force applicator, the rigid back structure of the thermal cell, cannot press through the container to the contacted body tissue and thus a high degree of conformation to the thermal receiving surface is obtained with a low pressure per unit area. Similarly when the thermal cell is applied to a target body region from below the weight of the thermal fluid is broadly supported by the substantially rigid shell or plate of the device thereby preventing slumping of the fluid away from the body surface. Thus, in this case the applied force to the body surface is only slightly larger than is required to support the weight of the thermal cell. The concave surface of the more rigid portion of the thermal cell places a greater volume of the internal heat transferring medium thereof against the body surface so that heat transfer to the target region is more efficient. Also the large concave surface of the rigid portion of the thermal cell provides for efficient containment of a greater volume of heat transferring medium, thus enabling longer therapeutic maintenance time before the heat or cold medium thereof must be replaced or restored.

Each of the compliant cells is defined by a substantially rigid cup-like shell structure which is preferably of oval configuration, but which may have any desirable configuration. The shell structure defines a contiguous lip or rim and further defines a filling opening which may be internally or externally threaded if desired. To the contiguous lip or rim of the shell is fixed the perimeter of a compliant diaphragm which is preferably in the form of a quite thin membrane composed of any one of a number of acceptable flexible liquid impervious materials having efficient thermal transferring characteristics and having the capability of readily conforming to the surface configuration of a target anatomical region such as a facial surface. For example, the compliant diaphragm may be composed of any one of a number of flexible polymer materials, natural or synthetic rubber or composites thereof. The compliant diaphragm has the capability of conforming to the surface configuration of the target region so that the heat or cold of the liquid constituent disposed therein will be efficiently transferred to the target region. The heat transferring liquid constituent may comprise water or other fluid and it may take the form of a chemical mix or controlled temperature release gel. The heated or cooled liquid constituent is poured through the filling opening into the internal chamber which is cooperatively formed by the shell and the compliant diaphragm. The compliant cell is then closed with a sealed closure cap which may be threaded into or over the filling opening depending upon the design thereof.

When the apparatus is assembled to the head of the patient the initially substantially flat heat/cold transferring surface of the compliant diaphragms of the cells will be deformed by the surface configuration of the target regions that are engaged thereby and, being retained in low mechanical pressure per unit area engagement with the target region by the headband structure, will release the heat or cold of the liquid or other material contained therein to the target regions.

The substantially rigid rear portion of the thermal cell may also be in the form of a plate of substantially flat configuration if desired. In this case the outer periphery of the plate may be of substantially the same dimension as the dimension of the compliant thermal transferring wall of the front portion of the thermal cell.

If desired the compliant cells may also be equipped to accomplish heating or cooling of the liquid therein and thus may be employed for heat/cold transfer to the patient over therapy periods of long duration. This feature enables close temperature controlled heat/cold therapy of controlled duration to thus be made possible according to the teachings of the present invention.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

In the Drawings

FIG. 5 is an elevational view of the rigid shell portion of the thermal cell structure of FIG. 4. structure thereof.

FIG. 6a is an isometric illustration of the support yoke portion of the preferred embodiment of the present invention.

FIG. 6b is a partial isometric illustration showing the outer sleeve portion of the support headband assembly of the invention.

FIG. 6c is a partial isometric illustration showing a portion of one of the inner sliding band members of the headband assembly.

FIG. 6d is a partial isometric illustration showing a portion of the deformable band structure of the headband assembly.

FIG. 7 is an exploded isometric illustration of the various components of the headband assembly.

FIG. 12 is a sectional view representing an alternative embodiment of the present invention, being adapted for continuous liquid circulated heating or cooling of an anatomical target region.

FIG. 12a is a sectional view of a further embodiment of this invention showing a closure cap having an electrically energized resistance heater for heating thermal material within the thermal compartment of FIG. 12.

FIG. 12b is an electrical schematic illustrating an electrical thermal resistance, fuse protected circuit for the resistance heated embodiment of FIG. 12a.

FIG. 13 is a partial sectional view illustrating bonded connection of the compliant membrane to the rigid shell of the compliant cell and representing an alternative of this invention.

FIG. 14 is a sectional view of an alternative embodiment of the present invention is in the form of a thermal cell having a removable compliant membrane.

FIG. 15 is a sectional view of a further alternative embodiment of this invention in the form of a thermal cell having a substantially planar rear wall and cell support structure.

DETAILED DESCRIPTION OF PREFERRED EMBODIMENT

Figure 1:
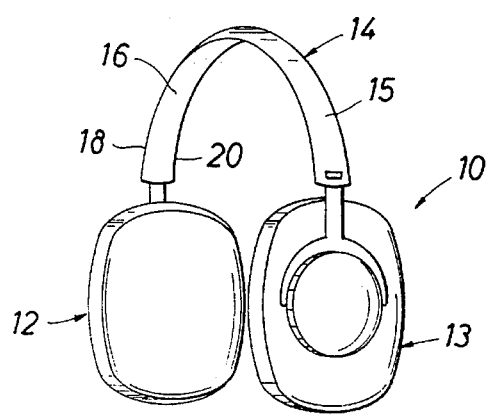
FIG. 1 is an isometric illustration of apparatus for application of heat/cold to the temporal is and masseter muscles of the human cranial anatomy and which is constructed in accordance with the present invention.

Referring now to the drawings and first to FIG. 1, apparatus is illustrated generally at 10 which represents a preferred embodiment of the present invention including thermal cells 12 and 13 which are capable of being utilized for simultaneous or selective application of heat or cold to the facial region of the human cranial anatomy, particularly at the temporalis and masseter muscles and to the facial area immediately surrounding the temporo-mandibular joint. For positioning and support of the thermal cells the apparatus 10 incorporates a headband assembly shown generally at 14 and incorporating a generally U-shaped, fairly wide headband 15 which is adapted to fit comfortably over the cranium of the user. The U-shaped headband is preferably constructed of polycarbonate or vinyl material which is molded or otherwise formed to define a wide head engaging surface 16 and smoothly curved edge surfaces 18 and 20.

The headband structure 14 is designed for movable support of the thermal cells so that they will respond to the surface configuration of the target region and establish intimate heat/cold transferring relation therewith. The thermal cells may be liquid containing, sealed, compliant cells shown generally at 12 and 13 which are adapted to engage the facial region of the cranial anatomy at selected locations and to transfer heat or cold from the respective compliant thermal cells to the selected facial regions. As is evident from the partial sectional view of FIG. 4, each of the liquid filled and sealed compliant cells is provided with a capability of thermochromics in that one of the wall structures thereof, i.e. the flexible substantially planar compliant wall 43 is designed for efficient, controlled heat/cold transfer from a liquid or semi-liquid material within the thermal cell to the facial anatomy of the user or to another selected target region of the users' anatomy.

As shown in FIG. 5, the compliant cell 22 is defined by a light weight, substantially rigid shell 26 which is preferably of polymer composition, being composed of a polymer such as ABS or any one of a number of suitable polymer materials. Even under circumstances where the rigid shell is composed of a polymer material, to minimize heat transfer therethrough, it may be of double-wall construction or may be provided with an internal layer of thermal insulation material. The rigid shell structure 26 defines a relatively large fill opening 28 which, as shown in FIG. 5, is defined by externally threaded wall structure 30 having threads 31 which are adapted to receive an internally threaded closure member 32. To facilitate threading and unthreading of the closure member 32, it may be provided with an external annular portion 34 having a roughened circular periphery 36 which is defined by multiple ridges and grooves molded or otherwise formed thereabout. Under circumstances where the wall structure 26 is insulated by an internal isolating layer 27, the closure member 32 may also be provided with an internal thermal insulating layer 33.

Figure 2:
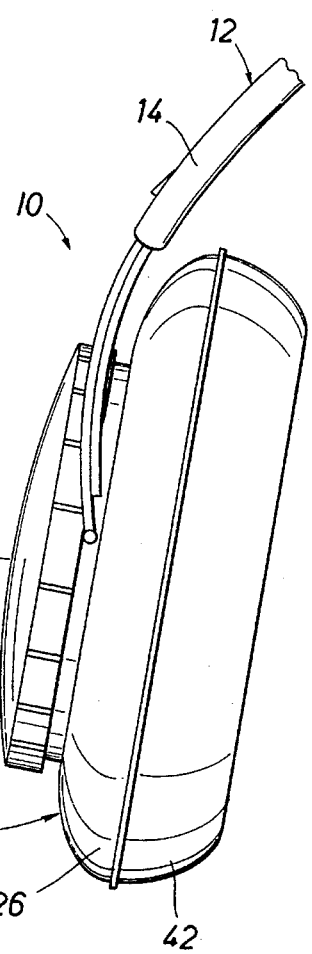
FIG. 2 is a partial side elevational view of the apparatus of FIG. 1 illustrating use of the apparatus in the application of heat/cold to an upper part of the facial anatomy of a human subject being partially illustrated by broken lines.
Figure 3:
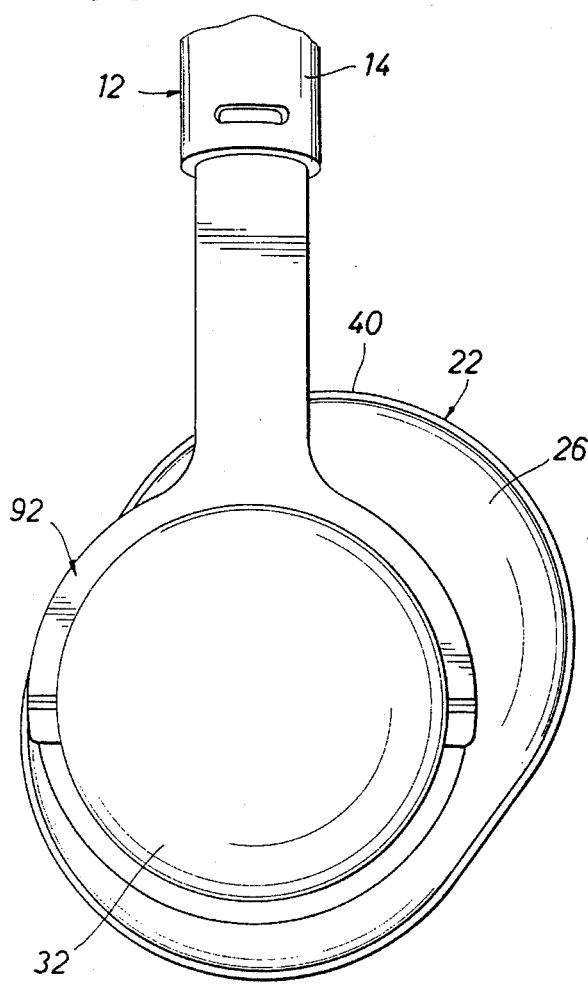
FIG. 3 is an elevational view of the face engaging heat/cold thermal compliant cell of the apparatus of FIGS. 1–3 for illustration of the manner by which the thermal compliant cell may be rotationally oriented relative to the headband support thereof for intimate heat/cold transferring engagement with a desired target region of the anatomy.
Figure 4:
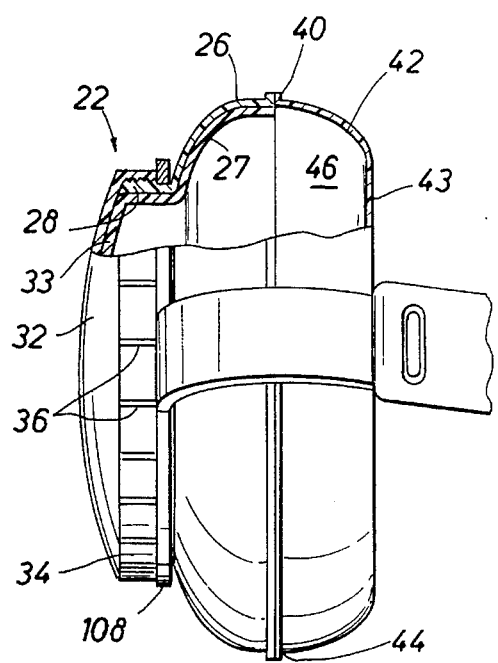
FIG. 4 is a partial sectional view of a thermal cell structure which embodies the present invention.

The rigid shell structure 22 is preferably of oval or somewhat elliptical configuration as is evident from FIGS. 2–4 and defines a peripheral edge flange 40. A thin, heat transferring compliant diaphragm or membrane 42 is provided with an edge portion 44 which is bonded or otherwise fixed to the edge portion 40 of the rigid shell. The membrane 42, which is quite thin and flexible, is composed of any one of a number of suitable liquid impervious materials such as natural or synthetic rubber or any one of a number of suitable flexible polymer materials such as polyvinylchloride (PVC). The membrane 42 cooperates with the rigid shell 26 to define a liquid containing chamber 46 which is filled by pouring through the fill opening 28 heated or cooled liquid material such as water or any suitable controlled heat releasing liquid composition or semi-liquid gel composition. The liquid or gel composition within chamber 46 may also take the form of any one of a number of suitable heat/cold generating or liberating materials that can prolong the duration of heat/cold therapy. From the standpoint of heat capacitance, the temperature of the contact surface of the compliant film bladder 42 should hold to a range of from about 128°–140° F. for approximately ten minutes while the device is being utilized for heat application under circumstances where the device is not provided with an internal heat source to maintain a desired temperature range. The temperature of the contact surface of the compliant bladder should hold to a range of from about 32° to about 40° F. for a period of about ten minutes while the device is being utilized for the purpose of facial cooling. If a liquid cooling system is employed, cooling can be maintained within any selected temperature range within the capability of the cooling system. Likewise, for heat therapy the heat source that is utilized for heating of the liquid or gel within the chamber 46 will control the temperature of heat application to the anatomical target region.

It is desirable to support the compliant thermal cells in substantially immovable relation with the cranial anatomy or other selected anatomical region and to provide for selective location thereof in contact with the facial surface at any selected one of a wide range of facial target regions. For example, the compliant cells may be supported for heating or cooling of the facial region immediately about the temporo-mandibular joint or may be selectively located for heating or cooling of the temporalis or masseter muscles depending upon the needs of the user. As shown in FIG. 2, the compliant cell 22 is positioned substantially at its uppermost location relative to the headband structure, such as for application of heat or cold to the temporalis muscles. The thermal compliant cell 22 is also sufficiently adjustable relative to the headband structure, such that it may also be positioned for application of heat or cold to the masseter muscles of the user. This wide range of positioning adjustment is also important when the thermal cells are supported for thermal therapy of other target regions of the human anatomy.

Figure 8:
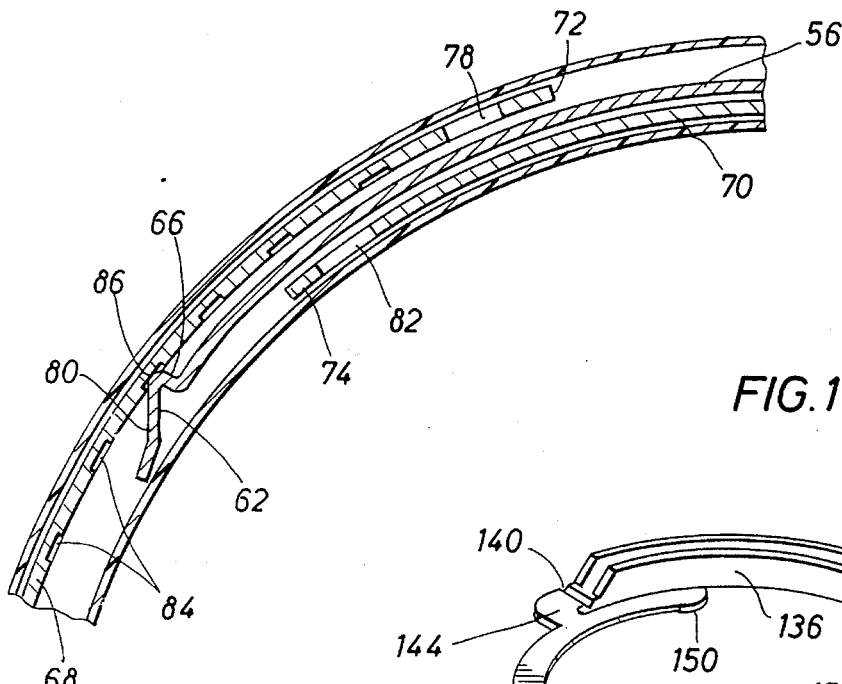
FIG. 8 is a partial sectional view of a portion of the headband assembly for illustration of the operative relationships of the headband components.
Figure 10:
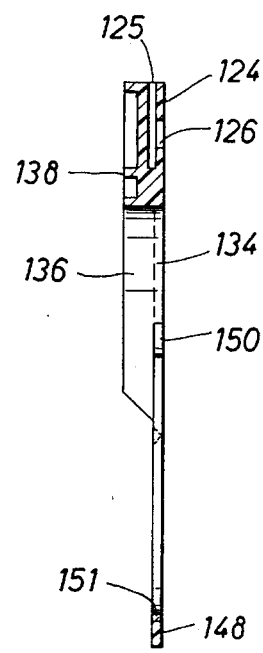
FIG. 10 is a sectional view taken along line 10—10 of FIG. 9.

For selectively position of support of the thermal cells and to achieve the wide range of support band adjustability that is appropriate for positioning of the compliant cells at the upper or lower facial regions of the cranial anatomy, the headband structure 12 will typically take the form that is shown in FIGS. 6a–6d and also shown in FIGS. 7 and 8. The headband structure shown generally at 14 will typically incorporate a curved crown piece 48 which is of flexible nature and which may be composed of sheet material such as vinyl which is heat sealed along side edges 50 and 52 to thus define a rather flat flexible sleeve structure defining an elongate internal chamber 54 having openings at each extremity thereof. Within the chamber 54 is located an elongate deformable band 56 which will typically be composed of a rather soft metal which is capable of being bent to a suitable configuration so as to fit the head of the user. The deformable band may be composed of any other suitable material such as a polymer having the capability of being bent to a suitable curved configuration and remaining at the desired configuration. The deformable band 56 defines opposed extremities 58 and 60 which will typically be located within the elongate internal chamber 54 of the crown piece 48. The deformable band 56 also defines stop members 62 and 64 at or near respective extremities thereof. As shown in FIG. 7 and as is also evident from FIG. 8 the stop member 62 may be defined by a structural deformation of the band structure 56 which defines a stop shoulder 66. The stop member or projection 62 is oriented to face upwardly as shown in FIG. 10 while the stop member 64, being of the same configuration, is oriented to project downwardly from the deformable band structure 56.

The deformable band 56 enhances the length of adjustment that can be made in the headband structure for relatively wide positioning of the compliant thermal cells at selected facial regions of the user. A pair of elongate support members or bands 68 and 70 are positioned with upper extremities thereof within the elongate chamber 54 of the crown piece 48 and in lapped relation with the deformable band 56. The adjustable support member 68 defines an upper extremity 72 which is located within the chamber 54 and which is disposed in overlapping relation with the deformable metal band 56. Similarly, the elongate support band 70 includes an upper portion 74 that is also disposed within the internal chamber 54 and is disposed in underlapped relation with the deformable metal band 56. When the adjustable support members 68 and 70 are retracted to the maximum extent thereof, they extend almost the entire internal length of the internal chamber 54 of the crown piece 48. Likewise, when fully extended the upper ends 72 and 74 of the respective thermal cell support members 68 and 70 remain within the internal chamber 54 with a majority of the respective support members being extended from the chamber 54 for maximum downward positioning of the compliant thermal cells relative to the facial regions of the users' cranial anatomy. At or near its upper end the support element 68 defines a stop member 76 which is disposed for stopping inter relation with stop member 62 of the deformable band at the maximum extended position of the support member. The stop member 76 may be in the form of an opening as shown at 78 in FIG. 10 for the purpose of receiving the stop member 62 and positioning the stop shoulder 66 in stopping relation with the upper portion of the support 68. To insure release of the stop 62 from the opening 78 the stop member 62 defines an external tapered cam surface 80. When linear force is applied to the support member 68 the cam surface 80 will disengage the stop projection 62 from the opening 78, thus allowing the support member to move toward its collapsed position. The opposite support member 70 defines a stop opening 82 which is adapted to receive the stop projection 64 in a maximum extended position of the support member so as to stop movement of the support member relative to the deformable metal band at the maximum extended position thereof. Thus, the support bands 68 and 70 cannot become inadvertently separated from lapped assembly with the deformable metal band even when extended to the maximum positions thereof. As the support bands are collapsed they can be extended to a substantially completely overlapped or underlapped relation with the deformable metal band as the case may be. This feature permits a wide range of adjustment or extension of the support bands 68 and 70 relative to the other components of the headband structure.

It may be desirable to provide for intermediate restraint and positioning adjustment of the support bands 68 and 70 relative to the crown piece 48 and the deformable metal band 56. One suitable means for accomplishing this feature may conveniently take the form of a plurality of internal adjustment depressions 84 which are defined in or on the respective support bands. As shown in FIG. 10 the depressions 84 are oriented for receiving the maximum curved extent 86 of the stop projection 62 depending upon the relative position of the support band relative to the deformable metal band. For example, the recesses or projections which may be embossed on the band 84 may be positioned ½ inch apart to provide successive click stops. If an adjustment of 2½ inches is desired, the user can simply move the band 68 or 70 7 click stops from the fully collapsed position.

It is desirable to establish a substantially omnidirectional supporting relationship between the headband structure and the respective thermal-compliant cells. One suitable means for accomplishing this feature may conveniently take the form shown in FIGS. 6a-6c and 7. As shown, the elongate support member or strip 68, which is composed of a spring-like material such as spring steel or any one of a number of suitable polymer materials having spring-like characteristics, such as high impact polystyrene for example, is provided with a bent lower segment 88 defining a retainer projection 90. A yoke member shown generally at 92 is provided for establishing connection with the bent terminal portion 88 of the spring-like sliding member 68. The yoke device 92 may conveniently take the form shown in FIG. 6a or, in the alternative, it may take the form shown in FIGS. 9-11. As shown in FIG. 6a the yoke 92 defines an upstanding projection 94 defining an internal receptacle 96 of a configuration receiving the retainer portion 88 of the band 68 and its retainer projection 90 in locked, but releasable connection therewith. The upstanding projection is integral with an arcuate yoke support 98 defining bifurcated extremities 100 and 102. These bifurcated extremities are integral with lateral support projections 104 and 106 that extend from opposite sides of a circular yoke connector element 108. The connection between the bifurcated extremities 100 and 102 of the arcuate yoke support 98 and the lateral projections 104 and 106 is in the form of a relatively thin and flexible connection which permits the yoke connector element 108 and the yoke support 98 to have a hinged relationship at 110 and 112. The yoke connector element 108 is therefore pivotally connected by the hinge sections 110 and 112 to the yoke support 98 thus permitting the thermal cell that is in assembly with the yoke connector element to also have pivotal support by the bifurcated yoke support 98 and by the spring-like sliding band 68 to which the yoke 92 is coupled.

As is evident from FIGS. 4 and 5 a circular retainer lip or flange 114 is defined by the externally threaded projection 30 of the rigid shell structure 26. The dimension of the flange or lip 114, relative to the dimension of the yoke connector element 108, is such that the yoke connector element can be forced past the flange or lip 114 whereupon it comes to rest within a circular external channel 116 that is defined between the flange 114 and the outer surface of the rigid shell 26. Installation of the yoke connector element 108 within the annular groove or receptacle 116 is typically made possible by the fact that the yoke connector element, being composed of a polymer material such as polypropylene, will yield to some extent as it is forced over the retainer flange 114. When in registry with an annular groove 116 the yoke connector element will contract to its original dimension, thus fitting snugly within the annular groove 116 and providing efficient support for the thermal cell. It should also be noted that the yoke connector element 108, though being snugly received within the circular groove 116, provides rotatable support for the thermal cell. Thus, the thermal cell, which may be of oblong configuration if desired, may be rotated to any angular position relative to the headband support structure, such as shown in FIG. 4, for example. Further, this rotational capability, together with the pivotal capability established by the integral hinge sections 110 and 112 permits the thermal cell to have a substantially omnidirectional supported relationship with the headband structure. This feature enables the thermal cell to readily be positioned rotationally according to the configuration of the target region of the facial anatomy of the user and to be readily pivoted to a position causing the flexible thermal transfer membrane 42 to achieve optimum thermal transmitting engagement with the surface configuration of the users' facial anatomy. In addition to rotation and pivoting as shown and described in connection with FIGS. 4 and 7, the yoke 92 may also have the capability of being twisted relative to the headband structure as shown in FIG. 5 to provide for further omnidirectional orientation capability of the thermal cell.

Figure 11:
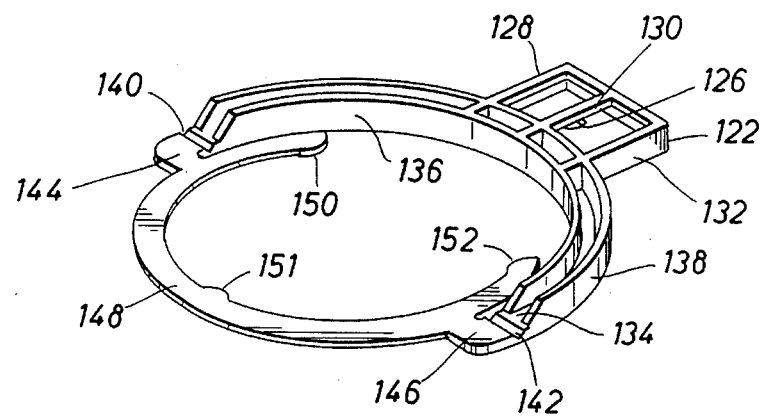
FIG. 11 is an isometric illustration of the yoke structure of FIGS. 9 and 10.
Figure 9:
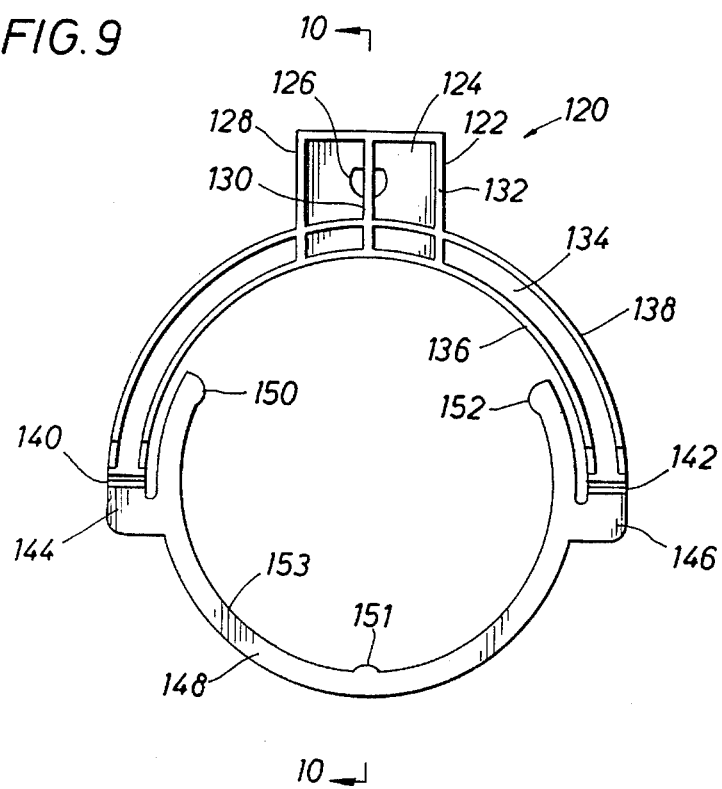
FIG. 9 is a front elevational view of a yoke structure representing an alternative to the yoke shown in FIG. 6 and which constitutes a position of the preferred embodiment.

Referring now to FIGS. 9-11, the yoke structure may conveniently take the alternative form shown generally at 120 wherein a box-like upstanding projection is provided as shown at 122 which incorporates a side plate 124 defining a releasable connector 126 and incorporating a plurality of vertically oriented ribs as shown at 128, 130 and 132 which provide the support structure 122 with adequate structural integrity without unnecessarily increasing the volume of material from which it is composed. The central rib 13 is spaced from the rear wall and will flex as the headband support 88 is inserted into the slot 125 thereof to permit the retainer projection 90 to establish interlocking within the locking opening 126. Typically the entire yoke 120 will be a molded item and will be injection or otherwise molded from a polymer material such as polypropylene.

Projecting downwardly and arcuately from the upstanding support projection 122 the yoke is an arcuate plate structure 134 having internal and external arcuate ribs 136 and 138 which cooperate with the plate 134 to provide sufficient structural integrity for efficient support of a thermal cell. The internal and external ribs will typically be tapered at their terminal extremities to permit efficient hinging of the thermal cell in the area of integral hinged sections 140 and 142 which are defined by V-shaped grooves to permit their hinging capability. Below the respective hinges the yoke structure defines a pair of integral lateral projections 144 and 146 to which is integrally connected an arcuate yoke connector element 148. The yoke connector dement is of C-shaped configuration extending arcuately through about 220 degrees and being provided with inwardly directed retainer bosses 150 and 152 at respective opposed extremities of the yoke connector element and an intermediate inwardly directed retainer boss 15 1. When the C-shaped yoke connector is in place within the retainer groove 116 of the thermal cell shown in FIG. 5, the projections 150, 151 and 152 each establish point contact with the cylindrical bottom surface of the retainer groove and minimize frictional engagement therebetween. This feature ensures that the thermal cell is readily rotatable relative to the yoke. As the yoke is brought into assembly with the thermal cell the yoke connector element 148 is moved laterally into the groove 116 defined between the retainer flange 114 and the external wall surface of the rigid shell of the thermal cell. During this movement the inwardly directed bosses 150 and 152 of the yoke connector extremities will engage the cylindrical internal surface of the retainer groove. Since the yoke connector element is composed of a relatively flexible material such as polypropylene the opposed bosses will be spread by cam-like activity thereby allowing the yoke connector element to move into fully received relationship within the retainer groove 116. The yoke connector element, after passing over the widest dimension of the retainer groove, will snap into place and will remain in supporting engagement with the rigid shell structure of the thermal cell with the projections 150, 151 and 152 establishing point contact with surface 116 of the thermal cell, thus spacing the inner peripheral surface 153 from the surface 116 of the retainer groove.

Referring now to FIGS. 12 and 13 there is illustrated an alternative embodiment of the present invention as shown generally at 154 which includes a generally rigid cell structure 156 to which is sealed a compliant heat transferring membrane 158 by sealed peripheral attachment or by any other suitable means of assembly. As indicated in detail in FIG. 13 the oval rim 160 of the shell 156 is formed to define a tapered connection surface 162 which is preferably oriented at an angle of about 45° with respect to the oval rim surface 160. The thin and flexible compliant membrane 158 is sealed at its respective oval edge to the tapered connection surface 162. This sealing arrangement may be accomplished by bonding such as be means of a polymer bonding material or by any other suitable means of attachment. It is important that the seal between the membrane 158 and the tapered surface 162 of the shell structure 156 be resistant to the heat transferring liquid that is contained within the internal chamber 164 of the compliant cell. The rigid shell structure 156 defines an outwardly projecting circular portion 166 having external threads 168 for threaded attachment of a closure cap 170 thereto. The closure cap is sealed with respect to the projecting portion 166 by means of a circular sealing dement 172.

It may be desirable to provide the compliant cell structure 154 with the capability of substantially continuous heating or cooling, thus allowing the user to comfortably utilize the device for its intended purpose over long periods of therapeutic use, without necessitating frequent changing of the heating or cooling liquid within the chamber 164. In this ease, the closure cap structure 170 may be provided with bosses 174 and 176 defining respective liquid transfer passages 178 and 180. The bosses 174 and 176 each define connectors which enable liquid supply tubes 186 and 188 to be connected in assembly therewith. Liquid from a suitable source S of heated or cooled liquid is circulated through the supply tube 186 and through the inlet passage 179 under the influence of a pump P. Liquid will then be continuously discharged from the chamber 164 via discharge passage 180 and the discharge tube 188 after which it may be conducted to an appropriate sump or reservoir R which may be interconnected with the supply source S. The supply source S may be provided with heating or cooling coils as shown at H and C and may also be provided with a temperature controller T to insure that the temperature of the liquid is controlled to a selected temperature range for the particular therapy that is to be accomplished. The thermal cells may be converted from the variety of FIG. 4 to the continuously heated or cooled variety by simply changing out the closure cap.

Referring now to FIGS. 12a and 12b the thermal cell 156 of FIG. 12 may be provided with electrically energized resistance heating simply by changing out the closure caps 170 of FIG. 12 and replacing it with a closure cap 171 as shown in FIG. 12a. The closure cap 171 is provided with an internal resistance heater 173 which is supported by a heater support structure 175 which may be assembled to or integrally connected with the closure cap. The resistance heater 173 will typically be provided with a liquid resistant cover surrounded an electrically heated resistance element which is shown schematically at 177 in FIG. 12b. The resistance element is coupled within an electrical circuit 179 having a circuit control thermostat 181 in the form of a thermally controlled fuse or any other suitable circuit protector. Externally of the closure cap 171 the electrical 179 is coupled with the output leads of a transformer 183 having its input circuit 185 deriving its electrical energy from a conventional source of alternating current via a connector plug 187. The transformer 183 may be coupled with the closure cap structure 171 or if desired it may be provided at any suitable location along the length of the supply circuit 185. The transformer 183 provides low voltage electrical energy for safe and efficient operation of the resistance heater 177.

Referring now to FIG. 14, it may be desirable to provide a thermal cell construction having a closed compliant membrane defining an internal compartment containing any suitable thermal release material and being separatable from a generally rigid shell structure comprising a compliant membrane receptacle. As shown in FIG. 14 an alternative embodiment is illustrated generally at 190 and includes a generally rigid shell 192 having a peripheral rim 194 that is provided with a suitable connector structure such as external threads 196. The generally concave shell structure 192 defines an internal compliant membrane receptacle 198 against which may be seated a rear wall portion 200 of a closed compliant membrane cell structure shown generally at 202. The compliant membrane shell structure may define a peripheral side wall section 204 and a substantially flat front wall section 206. If desired, the front wall section 206 may be of considerably less thickness as compared to the rear wall section 200. All of the walls 200, 204 and 206 may be flexible, with the rear wall 200 being supported by the concave surface 200. The compliant membrane cell 202, with its rear wall, side wall and front wall sections defines a closed cell structure forming an internal chamber 208 that may be filled with any suitable thermal release liquid material such as water, chemical release material, etc. The compliant cell structure 202 is composed of any suitable flexible material of rubber like characteristics. It may be composed of any suitable polymer material such as described above in connection with compliant membrane 158 as shown in FIG. 12. The compliant thermal cell 202 may define an integral intermediate peripheral retainer flange 210 which may be engaged by the retainer flange portion 212 of a threaded retainer 214 to releasably secure the compliant thermal cell 202 in seated assembly within the receptacle 198. The retainer element 214 defines a central opening 216 through which a front portion of the compliant thermal cell 202 projects so as to expose a portion of the side wall 204 and the thin front compliant wall 206 of the closed thermal cell for intimate heat/cold transferring contact with a target region of the human anatomy. The specific structure shown in FIG. 14 is intended only as a suitable embodiment of this invention and may have other desirable configuration without departing from the spirit and scope of this invention. Basically, the embodiment of FIG. 14 constitutes a closed, completely flexible or pliable cell containing thermal release material and being supported at rear and side wall portions thereof by a substantially rigid shell structure with a compliant front wall portion thereof exposed for thermal transferring contact with a target region of the human anatomy.

A rear portion of the rigid cell structure 192 may be of similar construction as shown and described above in connection with FIGS. 4 and 12. A circular projection 218 may extend rearwardly from the rigid shell 92 and may be provided with external threads 220 for receiving the internally threaded section 222 of a closure tap 224. The circular projection 218 may also define an annular stop flange 226 that is spaced rearwardly from the rigid cell structure 192 so as to define a circular groove 228 within which the retainer of a support yoke may be received to permit rotatable support of the thermal cell structure. Thus, the thermal cell shown in FIG. 14 may be supported by the yoke shown in FIG. 6a or the yoke shown in FIGS. 9–11.

For use, the flexible closed compliant cell 202 may be placed in heated or cooled water for heating or cooling thereof. After heating or cooling the cell 202 may be placed within the receptacle 198 and secured therein by means of the retainer 214. After this has been done the thermal cell assembly is ready for immediate use. When the closed thermal cell 202 has essentially lost its heating or cooling capability with respect to the target region it can be replaced with another heated or cooled compliant cell or the compliant cell may be again placed within heated or cooled liquid or other material to prepare it for reuse.

As shown in FIG. 15 a thermal cell representing an alternative embodiment of this invention is shown generally at 230 which incorporates a substantially planar rear wall 232 of generally rigid nature. The rear wall structure 232 defines a threaded opening 234 through which water or any other thermal release medium is poured into or from. The opening 234 is adapted to receive a threaded closure plug 236 which may also provide a support mount groove 238 similar to groove 228 of FIG. 14.

A compliant membrane 240 having side walls 242 and a front thermal transfer wall 244 is secured at its outer periphery 246 to the outer periphery of the rigid plate type rear wall 232 by means of bonding material or by any other suitable means of sealed attachment. The rigid wall 232 and compliant membrane 240 cooperate to define a closed chamber 250 which contains water or any other suitable thermal release medium.

The apparatus of the present invention, whether taking any one of the various embodiments thereof as shown in the drawings, provides a compliant cell structure which comprises a rigid backwall structure defining a peripheral rim and with a compliant heat transferring membrane defining a front wall for intimate engagement with a target anatomical region for therapeutic heat/cold transfer thereto. The compliant cell has the capability of being supported in desirably positioned assembly about the cranial anatomy of a user or any other selected target region of the anatomy so as to bring compliant heat transferring diaphragms into intimate conforming engagement with the surface configuration of the target region anatomy of the user. These cells may be adjusted upwardly or downwardly as shown in FIGS. 2 and 3 so as to selectively apply heat or cooling to desired areas of the facial anatomy. Liquid within the compliant cells is either heated or cooled so as to transfer heating or cooling to the temporalis or masseter muscles or to the temporo- mandibular joint as is desired for therapeutic activity. As an added feature, heated or cooled liquid may be circulated through the compliant cells to provide for heating or cooling therapy over long periods of time without necessitating disassembly of the apparatus from the head. The liquid may be heated or cooled in any desired manner and whether heated or cooled may be circulated through the compliant cell. As a further alternative the liquid within the compliant cell may be electrically or otherwise heated within the cell itself to thus provide for therapeutic heating or cooling over long periods of time.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than the foregoing description, and all changes which come within the meaning and range of the equivalence of the claims are therefore intended to be embraced therein.

What is claimed is:

1. Thermal cell apparatus for applying heat/cold to opposed target regions of the human anatomy, comprising:

(a) a headband adapted to be received over the head of the user and having adjustable thermal cell support means:

(b) a pair of substantially identical generally rigid shells having a concave internal surfaces each defining a thermal chamber for containing a substantially liquid heat/cold source and defining a threaded rim defining a filling opening, said generally rigid shells each defining a peripheral wall having a Connector rim located about said concave internal surface;

(c) a threaded closure being received by said threaded rim;

(d) a compliant membrane composed of thin flexible material having characteristics of efficient heat transfer and having an annular outer peripheral side wall being substantially contiguous with said peripheral wall of said generally rigid shell and being secured in sealed relation to said peripheral rim, said annular outer peripheral wall of said compliant membrane and being of substantially constant dimension from said peripheral rim to said substantially planar compliant wall and defining at least a portion of said thermal chamber and being adapted to contain said substantially liquid heat/cold source within said thermal chamber and defining a substantially planar readily yieldable external compliant wall being oriented substantially parallel to said peripheral rim and having the facility when urged with light mechanical pressure against the target region to conform intimately to the surface configuration of said target region and establish efficient heat/cold transferring relation therewith for transferring heat/cold of said substantially liquid heat/cold source to said target region; and (e) means supporting said generally rigid shells in rotatable relation with said adjustable thermal cell support means.

2. The thermal cell apparatus of claim 1, wherein:

said side wall portion of said compliant membrane is fixed and sealed to said peripheral rim by means of bonding material.

3. The thermal cell apparatus of claim 1, wherein:
said side wall portion of said compliant membrane is mechanically secured in releasable relation to said peripheral rim and is sealed thereto by mechanical pressure.

4. The apparatus of claim 1, including:
a retainer element adapted for releasable attachment to said peripheral rim of said generally rigid shell, said retainer element securing said compliant membrane in releasable, sealed relation with said peripheral rim.

5. The apparatus of claim 1, wherein:
(a) said generally rigid shell defines a peripheral rim having threads thereon; and
(b) said retainer having threads for threaded engagement with said threads of said peripheral rim and adapted for retaining engagement with said compliant membrane, said retainer further defining an opening through which a portion of said compliant membrane extends.

6. The apparatus of claim 1, wherein said target region is opposed portions of the human cranial anatomy and said headband further comprises:
(a) a generally curved tubular crown piece adapted for supporting engagement with the crown of said cranial anatomy and defining a pair of open ends and an internal chamber;
(b) a curved crown band being movably located within said internal chamber and having opposed ends located within said internal chamber and in spaced relation with respective open ends of said curved tubular crown piece, said crown band defining first and second end stops:
(c) a first thermal cell support defining a first part of said thermal cell support means and band having an inner portion thereof located for linear movement within said internal chamber and in overlapping relation with said curved crown band, said inner portion of said first thermal cell support band having an extension limit stop disposed for stopping engagement with said first end stop of said curved crown band upon full extension of said first thermal cell support band from said curved crown piece, said first thermal cell support band defining an outer portion having a first support connector;
(d) a second thermal cell support band defining a second part of said thermal cell support means and having an inner portion thereof being located for linear movement within said internal chamber and being disposed in underlapping relation with said curved crown band, said inner portion of said second thermal cell support band having an extension limit stop disposed for stopping engagement with said second end stop of said curved crown band upon full extension of said second thermal cell support band from said crown piece, said second thermal cell support band defining an outer portion having a second support connector; and
(e) first and second connector yokes being connected respectively to said first and second support connectors and establishing hinged and rotary support connection with respective ones of generally rigid shells of said thermal cells.

7. The apparatus of claim 6, wherein:
said first and second connector yokes are disposed in said releasable connection with respective ones of said first and second support connectors.

8. The apparatus of claim 6, wherein:
said extension limit stops of said curved crown band are defined by bent sections at respective extremities;
said curved crown band, one of said bent sections defining a stop shoulder projecting toward said first thermal cell support band and the other of said bent sections defining a stop shoulder projecting toward said second thermal cell support band.

9. The apparatus of claim 8, wherein:
said bent sections projections in opposed lateral directions.

10. Thermal cell and cell support apparatus for applying heat/cold to a target region of the human cranial anatomy and adapted to contain a substantially liquid source of heat/cold, comprising:
(a) a generally rigid thermal insulating shell defining a threaded rim defining a full opening and further peripheral rim;
(b) a compliant membrane composed of thin flexible efficient heat transferring, liquid impervious material and having a generally planar thin compliant wall of less thickness than the thickness of said generally rigid thermal insulating shell and an integral peripheral side wall being substantially contiguous with said peripheral rim and being oriented in substantially normal relation with said thin compliant wall and being of substantially constant dimension from said peripheral rim to said thin compliant wall and being connected in sealed relation to said peripheral rim and cooperating with said generally rigid shell to define an internal liquid containing thermal cell chamber, said thin compliant wall of said compliant membrane adapted, when positioned against said target region, to conform intimately to the surface configuration of said target region and establish efficient heat/cold transferring relation therewith;
(c) a headband structure adapted to extend over the head of the user and having a thermal cell support member adjustably connected thereto; and
(d) yoke means connected to said support thermal cell member and supporting said generally rigid thermal insulating shell for movement relative to said support member thus permitting user adjustable positioning of said compliant membrane in intimate thermal transmitting engagement with said target region.

11. The apparatus of claim 10, including:
a quantity of thermal release liquid being disposed within said internal chamber and, upon engagement of said compliant membrane with said target region of the human anatomy, transferring heat or cold through said compliant membrane to said target region.

12. The apparatus of claim 10, including:
means for circulating temperature controlled liquid through said internal chamber to thus maintain the temperature of liquid therein within a desired temperature range.

13. The apparatus of claim 10, including:
means for maintaining liquid within the said internal chamber within a desired temperature range.

14. The apparatus of claim 10, wherein said yoke means comprises:
(a) a connector element adapted for supporting connection with said generally rigid shell; and
(b) a support strap having pivotal connection with said connector element and substantially fixed connection with said support member of said headband structure.

15. The apparatus of claim 14, wherein; said support strap is integral with said connector element.

16. The apparatus of claim 10, wherein:

(a) said generally rigid shell defines a circular retainer receptacle; and said connector element being rotatably received within said circular retainer receptacle and with said pivotal connection thus permits substantially omnidirectional positioning of said compliant structure to permit ease of intimate engagement thereof with said target region.

17. The apparatus of claim 10, wherein said headband structure defines an anatomical support band construction for supporting and providing for wide selective positioning of said generally rigid thermal insulating shell and said compliant membrane and comprises:

(a) an elongate sleeve member defining an internal chamber and defining first and second open ends;

(b) a guide band defining opposed sides and opposed ends and being located within said internal chamber, said guide band having an extension stop element at one of said opposed ends thereof; and (c) a support band being linearly movable between extended and collapsed positions relative to said elongate sleeve member and having an inner portion thereof movably received within said internal chamber and in sliding lapped relation with one of said opposed sides of said guide band, said support band having a stop element disposed for stopping engagement with said extension stop element of said guide band in the fully extended position thereof said support band being movably connected to said generally rigid thermal insulating shell for support thereof.

* * * * *